United States Patent [19]

Landry, Jr. et al.

[11] Patent Number: 5,127,906
[45] Date of Patent: Jul. 7, 1992

[54] NON-REUSABLE SYRINGE

[75] Inventors: Maurice J. Landry, Jr., Nashua, N.H.; Frederick L. Plouff, Wakefield, Mass.

[73] Assignee: FLP Enterprises, Inc., Andover, Mass.

[21] Appl. No.: 679,323

[22] Filed: Apr. 2, 1991

Related U.S. Application Data

[63] Continuation-in-part of Ser. No. 344,992, Apr. 28, 1989.

[51] Int. Cl.$^5$ .............................................. A61M 5/00
[52] U.S. Cl. .................................... 604/110; 604/218
[58] Field of Search ............... 604/110, 187, 218, 220, 604/221, 228

[56] References Cited

U.S. PATENT DOCUMENTS

| | | | |
|---|---|---|---|
| 4,687,467 | 8/1987 | Cygielski | 604/110 |
| 4,699,614 | 10/1987 | Glazier | 604/110 |
| 4,713,056 | 12/1987 | Butterfield | 604/110 |
| 4,731,068 | 3/1988 | Hesse | 604/110 |
| 4,878,899 | 11/1989 | Plouff | 604/218 X |
| 4,915,692 | 4/1990 | Verlier | 604/110 |
| 5,021,047 | 6/1991 | Movern | 604/218 X |

*Primary Examiner*—John D. Yasko
*Attorney, Agent, or Firm*—Pearson & Pearson

[57] ABSTRACT

A single use syringe in the form of a cylindrical barrel with a port end attached to a hypodermic needle. A plunger and piston in the barrel transfer liquid into or from the syringe through a port end. The plunger includes a locking structure formed at a predetermined position. An insert at a remote end of the barrel includes at least one cantilevered, longitudinally extending resilient arm with a radially acting, inwardly extending follower at a free end thereof that rides over the plunger. When the plunger moves to a locking position, the follower engages the plunger locking structure to block any further longitudinal motion of the plunger and piston preventing any subsequent use of the syringe.

40 Claims, 6 Drawing Sheets

NON-REUSABLE SYRINGE

CROSS REFERENCE TO RELATED APPLICATION

This is a continuation-in-part of our copending application Ser. No. 07/344,992 filed Apr. 28, 1989 for a Non-Reusable Syringe that is assigned to the same assignee as the present invention.

BACKGROUND OF THE INVENTION

1. Field of the Invention

This invention is directed to syringes for medical use and more specifically to syringes that can be used only once.

2. Description of Related Art

Reference is made to the following Letters Patent of the United States
   U.S. Pat. No. 4,687,467 (1987) Cygielski
   U.S. Pat. No. 4,699,614 (1987) Glazier
   U.S. Pat. No. 4,713,056 (1987) Butterfield
   U.S. Pat. No. 4,731,068 (1988) Hesse
   U.S. Pat. No. 4,878,899 (1989) Plouff A syringe has several basic parts, namely: a barrel, a plunger and a piston. The barrel normally houses the piston and supports the plunger in the form of a push-rod, or the like, for moving the piston axially within the barrel The plunger exits the barrel at one end thereof The barrel supports a hypodermic needle or the like at the opposite end. In use, a person withdraws the plunger thereby moving the piston away from the needle and transferring medicine into a cavity formed between the needle end of the barrel and the piston. When the correct amount of medicine has been withdrawn, the needle is injected into a patient and the plunger is moved toward the needle end, forcing the medicine from the cavity through the needle into the patient.

In recent years considerable effort has been expended to provide a syringe for medical use that is both disposable and not reusable. Some of these syringes include a push-rod and piston that are detachably interconnected by some mechanical coupling or operator. The operator couples the push-rod and piston during an initial withdrawal to transfer medicine from a storage container into the syringe. When the push-rod moves toward the needle end during an injection, however, the operator decouples the push-rod and piston. Any attempt to withdraw the push-rod thereafter separates the push-rod and the piston, so additional medicine can not be transferred into the syringe. The Hesse and Glazier patents are examples of this approach.

In other syringes a mechanism affixed to the barrel captures the piston or the push-rod when all the medicine has been injected into a patient. This prevents any subsequent withdrawal of the push-rod so that no additional medicine can be transferred into the syringe. The Plouff and the Butterfield patents are examples of this general approach.

Syringes fill because a partial vacuum is produced within the syringe as the push-rod and piston are withdrawn during a filling operation. In the Cygielski patent, a cutter near the needle end of the syringe punctures a seal formed by the piston as a dose of medicine is administered to a patient. If the push-rod and piston are subsequently withdrawn, air leaks through the punctured seal so no partial vacuum forms and no medicine can transfer into the syringe.

Each of these proposed constructions have certain disadvantages. For example, the Plouff, Butterfield and Cygielski patents incorporate elements within the liquid cavity so these elements contact the fluid directly. This complicates the sterilization process. Including elements within the cavity complicates sealing construction and can lead to leakage. Syringes such as suggested by the Glazier and Cygielski patents contain mechanisms for achieving the one use objective. However, these mechanisms are somewhat complex and can increase manufacturing costs.

SUMMARY

Therefore it is an object of this invention to provide an improved syringe for medical use that can be used only once.

Another object of this invention is to provide a syringe for medical use that can be used only once and eliminates elements in the fluid cavity.

Yet another object of this invention is to provide a syringe for medical use that can be used only once in which the elements that prevent repeated use also limit the dose that can be drawn into the syringe.

In accordance with this invention, a syringe includes a cylindrical barrel means that supports a hypodermic needle at a port end thereof. Piston means define a fluid cavity between the port end of the barrel means and the piston means. A plunger means moves the piston means axially within the barrel mans over a range of positions displaced from a locking position. The plunger means has a first locking means formed therewith. An insert, affixed to and at least partially disposed in the barrel means remotely from the fluid cavity and coextensively with a portion of the plunger means, has a second locking means that rides over the plunger means during axial motion in the other positions. The first and second locking means engage when the plunger moves to the locking position thereby to block the plunger means from further axial motion so the syringe can not be reused.

BRIEF DESCRIPTION OF THE DRAWINGS

This invention is pointed out with particularity in the appended claims. The various objects, advantages and novel features of this invention will be more fully apparent from a reading of the following detailed description taken in conjunction with the accompanying drawings in which like reference numerals refer to like parts, and in which:

DESCRIPTION OF ILLUSTRATIVE EMBODIMENTS

Referring to FIGS. 1 through 5, a syringe 20 includes a cylindrical barrel 21 with a first, or port, end 22, a second, or remote, end 23 and a body portion 24. The first end 22 has a concave, conical shape that reduces from the diameter of the body portion 24 to smaller diameter at a hypodermic needle attachment 25 with a passage 26 (shown in FIGS. 2 through 5). The attachment 25 receives a hypodermic needle 27 with internal passages for the subcutaneous administration of a liquid.

Figure 1:
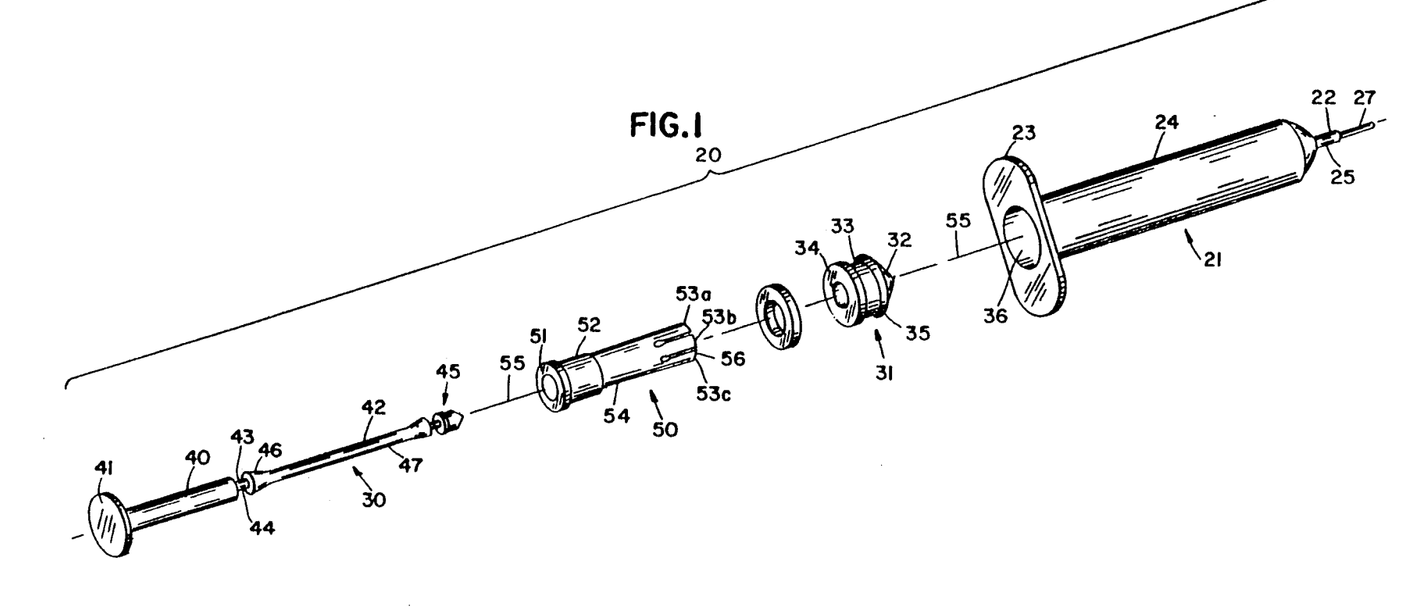
FIG. 1 is an exploded, perspective view of a barrel, plunger, piston and insert that are included in one embodiment of a syringe constructed in accordance with this invention.

The syringe 20 also includes a plunger 30 that carries a piston 31 within the barrel 21. The piston 31 has a convex conical end portion 32 that complements the inner concave surface of the barrel 21 at the first end 22. A body portion 33 on the piston terminates longitudinally with two annular protuberances 34 and 35 that form a sliding seal with an internal surface 36 of the barrel 21.

Figure 2:
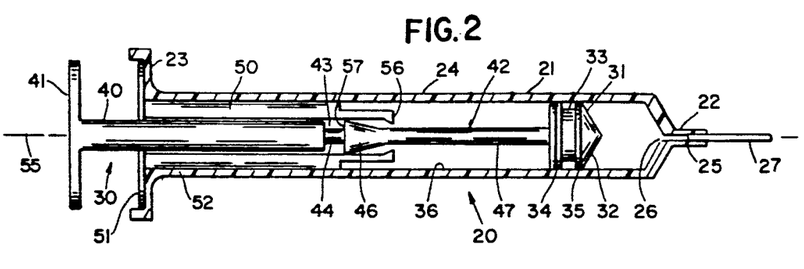
FIG. 2 depicts the syringe of FIG. 1 with the plunger positioned to begin filling the syringe.
Figure 3:
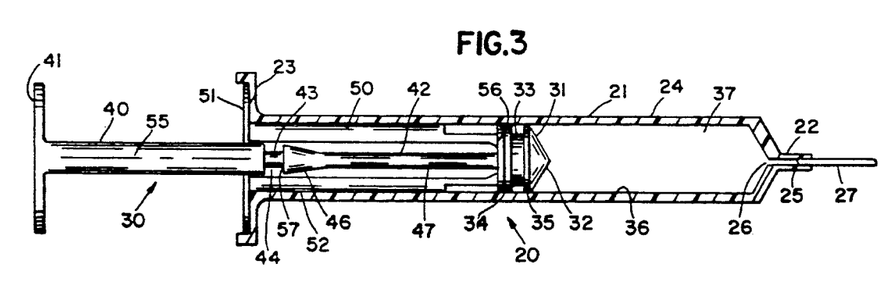
FIG. 3 is a view of the syringe in FIG. 2 in which the plunger is fully retracted.

As the plunger 30 moves from the position in FIG. 2 to the position in FIG. 3 during a filling operation with the hypodermic needle 27 in liquid, differential pressure forces the liquid through the needle 27 and passage 26 to fill a cavity 37. The cavity 37 increases in volume as the piston 31 moves toward the second end 23. When the plunger 30 then moves toward the first end 22, the piston 31 forces the liquid from the cavity 37 through the passage 26 and the needle 27. When the piston 31 reaches the first end 22, the convex portion 32 fits within the conical end portion 22 and thereby expels essentially all the liquid from the syringe 20.

In accordance with one embodiment of this invention, the syringe shown in FIGS. 1 through 5 is limited to one use by a locking mechanism that includes the plunger 30. In this specific embodiment the plunger 30 comprises a cylindrical push-rod 40 of a given diameter with an integral thumb pad 41. A cylindrical stem 42 is longitudinally aligned with and spaced from the push-rod 40 to form an intermediate detent area 43 in the form of a circumferential groove. A connecting stem 44 interconnects the push-rod 40 and the stem 42; the stem 44 may be formed integrally by molding or may comprise a central core member that is ultrasonically welded or otherwise affixed to the push-rod 40 and stem 42.

A free end 45 of the stem 42, shown in FIG. 1, engages the piston 31 with sufficient force to allow the stem 42 to withdraw the piston 31 and overcome the friction between the sealing protuberances 34 and 35 and the inner surface 36 of the barrel 21. The other end 46 of the stem 42 flares to a diameter of approximately the diameter of the push-rod 40. The diameter of an intermediate portion 47 of the stem 42 is slightly larger than the connecting stem 44 and less than the maximum diameter of the end portion 46.

The locking mechanism also includes a generally cylindrical insert 50 that comprises a cap 51, a body portion 52, and four longitudinally extending, circumferentially spaced arms 53a, 53b and 53c (the fourth arm does not appear in the views) that cantilever from a reduced diameter support portion 54 of the body. Each arm 53 can flex in a plane that is coplanar with each of the arms 53a, 53b and 53c and with a longitudinal axis 55 through the syringe 20. Each arm, such as arms 53a, 53b and 53c terminate, at their respective free ends, with radially acting, inwardly directed followers 56 that are biased toward the axis 55.

The syringe 20 is normally shipped as shown in FIG. 2 with the detent area 43 positioned inside a volume defined by the insert 50 as shown in FIG. 1. The thumb pad 41 and push-rod 40 then can be retracted to the position shown in FIG. 3 where the piston 31 abuts ends 56 of the insert 50. It will be apparent that the length of the insert 50 can be adjusted to control the volume of the cavity and thereby limit the quantity of liquid that can be withdrawn into the syringe. Moreover, in this position, the detent area 43 still lies within and is covered by the barrel 21 and the insert 50. Thus, it is not possible to access the detent area 43 to reduce the diameter of the flared end 46 in an attempt to defeat the locking mechanism.

Figure 4:
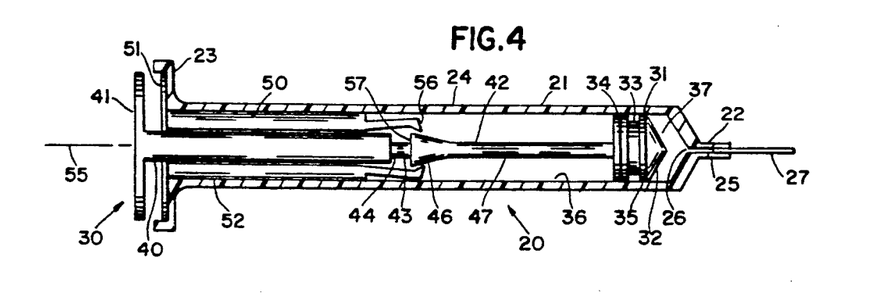
FIG. 4 is a view of the syringe shown in FIG. 2 with the plunger positioned just prior to completion of an injection.
Figure 5:
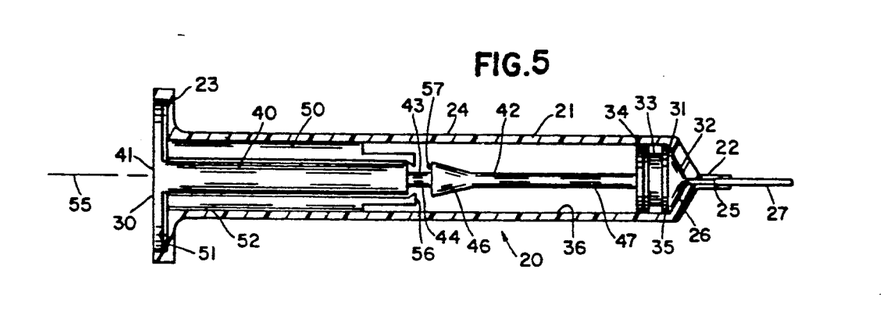
FIG. 5 is another view of the syringe in FIG. 2 wherein the insert clamps the plunger after use.

As the thumb pad 41 moves toward the end 22, the piston 31 ejects the liquid in the cavity 37 from the syringe 20, and the followers 56 attached to each of the arms 53 ride over the surface of the stem 42, as shown in FIG. 4. As they ride over the flared end 46, the arms 53 move outward to flex the material adjacent the support portion 54 and increase the bias on the arms 53. As the injection is completed and the piston 31 moves to the position shown in FIG. 5, the portion 46 passes to the right of the arms 53 whereupon the arms 53 snap, with an audible click, to a relaxed position as the followers 56 lock into the detent area 43. A radial end surface 57 on the stem 42 then overlaps the followers 56 and blocks motion of the plunger 30 if there is an attempt to retract it. At the same time, the thumb pad 41 rests within a recess of the cap 51 thereby to be flush with end 23 of the barrel. This makes it difficult to retract the plunger or even to grab it.

Figure 6:
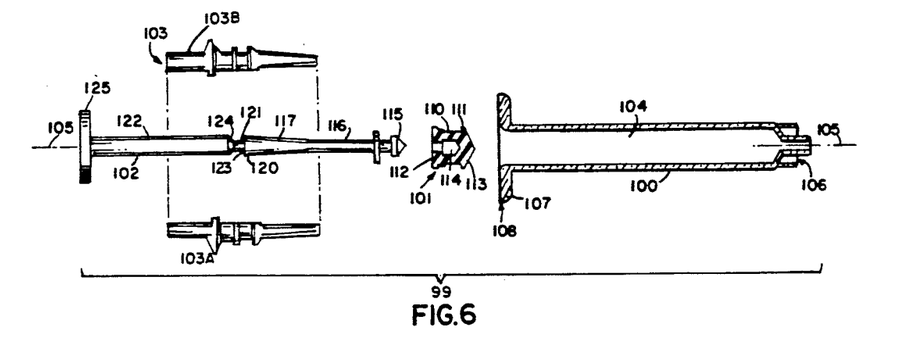
FIG. 6 is an exploded plan view of a barrel, plunger, piston and insert for another embodiment of a syringe constructed in accordance with this invention in which some of the elements are shown in cross section.

FIG. 6 is an exploded view of an alternative embodiment of a syringe 99 constructed in accordance with this invention. The syringe 99 includes, as basic elements, a cylindrical barrel 100, a piston 101, a plunger 102 and an insert 103 comprising identical semicylindrical components 103A and 103B. The cylindrical barrel 100 has a passage 104 along a longitudinal axis 105. The axis 105 extends through a port end 106 that normally includes both a conventional fitting for a hypodermic needle and protective cover and a leuer-lock fitting. The axis 105 also extends through a radial flange 107 at the other, or remote, end 108 of the barrel 100.

The piston 101 has a cylindrical body portion 110 and two radially acting, axially spaced circumferentially extending sealing ribs 111 and 112. Other sealing structures can be utilized in lieu of the two sealing ribs 111 and 112. A generally transverse, conical face 113 adjacent the sealing ribs 111 conforms generally to the interior of the port end 106. The piston 101 also contains a centrally located receptacle 114 for receiving a connecting structure 115 on the plunger 102.

The plunger 102 comprises, as additional elements displaced along the axis 105 from the connecting structure 115, a first cylindrical stem portion 116, a flared stem portion 117 that reaches a maximum diameter at location 120 adjacent a circumferential groove 121. The groove 121 is intermediate the flared stem 117 and a second cylindrical stem portion 122. The circumferential groove 121 is limited by a radial wall 123 and an axially spaced tapered wall 124. Typically the maximum diameter portion 120 of the flared stem portion 117 and the second cylindrical stem portion 122 have approximately the same diameters. The groove 121 and the walls 123 and 124 constitute a first locking means located on the plunger 102. The plunger 102 terminates with a transverse cylindrical thumb pad 125 or related structure.

Figures 7A, 7B:
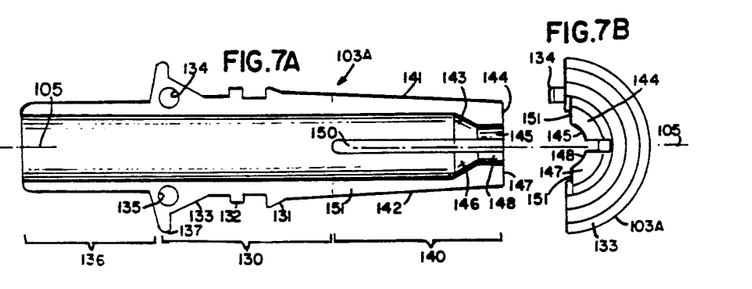
FIGS. 7A through 7D are four plan views of a component useful in forming the insert of FIG. 6.

As shown in FIG. 6, the insert 103 comprises two semicylindrical components 103A and 103B. As shown in more detail in FIGS. 7A through 7D, the component 103A has a central body portion 130 with a plurality of axially spaced, radially extending bands 131, 132 and 133. They locate and seal an assembled insert 103 within the barrel 100, as shown in FIG. 8. The band 131 is ramped to facilitate centering; the band 132 is rectangular to stabilize the insert 103 within the barrel 100; and the band 133 provides an enlarged body portion with a locating pin 134 on one side of the axis 105 and a oppositely disposed corresponding locating hole 135. A collar portion 136 extends axially from the central body portion 130, and an extended flange 137, at the junction of the central body portion 130 and the collar portion 136, covers the remote end 108 of the barrel 100.

The insert 103A includes another structure 140 that serves as a locking means for engaging the circumferential groove 121 in the plunger 102 of FIG. 6. More specifically the insert portion 103A has two longitudinally extending arms 141 and 142 that occupy two quadrants of a circle in cross-section as shown in FIGS. 7A and 7B. When installed in the barrel, the arms 141 and 142 extend toward the port end 106. Each arm has a radial projection at its free end for engaging the groove 121. More specifically the arm 141 has a radially acting, inwardly directed projection or follower 143 with a radial end surface 144 and a curved surface 145 that conforms generally to the cylindrical surface of the plunger 101. Similarly the arm 142 has a radially acting, inwardly directed follower 146 with a radial end surface 147 and a curved surface 148. In this particular component the arms 141 and 142 are bifurcated along an axial slot 150. As shown in FIGS. 7B and 7D, an upper surface 151 of the arm 142 lies in a plane that is slightly below and parallel to a plane through the longitudinal axis 105.

Each component, such as component 103A, shown in FIGS. 7A through 7D is easily molded with reasonable precision. Moreover, in accordance with this embodiment of the invention, two components, such as components 103A and 103B in FIGS. 6 and 8, are easily assembled into an insert 103. More specifically, it is merely necessary to position insert halves 103A and 103B about the plunger 102 and connect them with the locating pin 134 on one component (e.g., 103A) engaging the locating hole 135 on the other component (e.g., 103B). The resulting insert 103 has four radially spaced arms, such as arms 141 and 142, that provide four followers, such as followers 143 and 146, for engaging the circumferential groove 121.

As specifically shown in FIG. 6, the two halves 103A and 103B are initially located centrally with respect to the circumferential groove 121 thereby to be hold the plunger 102 and enable relative axial motion between the insert 103 and the plunger 102. The barrel 100 receives a subassembly of the piston 101, plunger 102 and insert 103 as shown in FIG. 8 to complete the syringe 99. The sealing rings 131, 132, and 133 engage interior portion surfaces of the barrel 100 and the sealing flange 137 abuts and overlies the portions of the flange 107. Moreover, the internal diameter at the collar portion 136 of the insert 103 corresponds to the diameter of the stem portion 122, so the insert 103 stabilizes the plunger 102 radially at the remote end 108 as the plunger 102 moves axially within the syringe 99.

Figure 9:
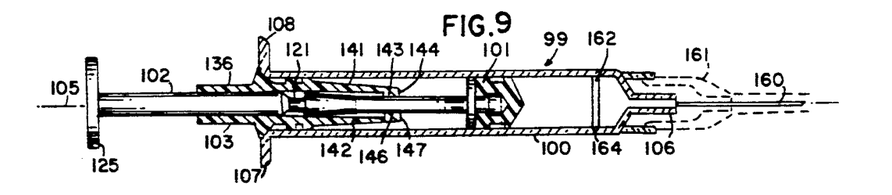
FIG. 9 is a view that depicts the syringe of FIG. 8 with its plunger and piston in an intermediate shipping location.
Figure 10:
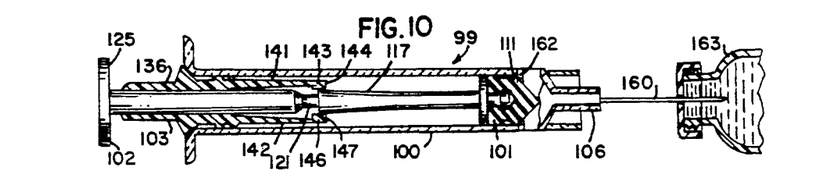
FIG. 10 is a view that depicts the syringe FIG. 9 with the plunger advanced prior to filling the syringe.
Figure 11:
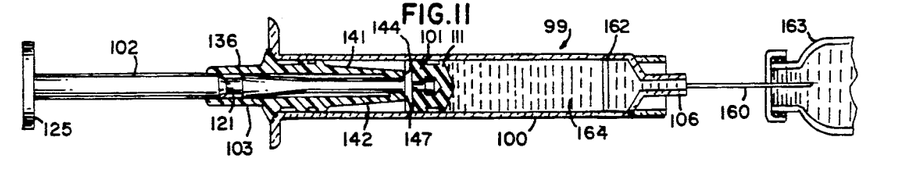
FIG. 11 is a view of the syringe in FIG. 9 when the plunger is fully retracted prior to administration of the contents of the syringe.

FIGS. 9 through 12 disclose the syringe 99 in a horizontal position for purposes of understanding its operation. In most circumstances the filling operation occurs with a vial 163, as shown in FIGS. 10 and 11, located above the syringe 99 in an inverted orientation.

In use the syringe 99, as shown in FIG. 9, has a hypodermic needle 160 and protective cover 161 attached at the port end 106 and shown in phantom in FIG. 9. The plunger 102 may be at the position shown in FIG. 9 or positioned so the piston 100 abuts the end surfaces 144 and 147. At this point the cover 161 can be removed and the hypodermic needle 160 inserted into a vial 163, as shown in FIG. 10.

During a filling operation pressure applied to the transverse pad 125 advances the plunger 102 and the piston 101 toward the port end 106 thereby to pressurize the liquid in the vial 163. This displaces the piston 101 and plunger 102 toward a first, or locking, position in which the piston 101 normally abuts the ends of the barrel at the port end 106. As shown in FIGS. 9 through 11, a graphical line 162 on the barrel 100 defines a position displaced slightly away from the first or locking position. During a filling operation, an individual stops advancing the plunger (to the right in FIGS. 9 through 12) when the piston 101 reaches a maximum displacement position defined by the graphical line 162. Referring to FIG. 10, this position occurs when the sealing rib 111 on the piston 101 aligns with the graphical line 162. At this point the followers 143 and 146 are riding on the flared stem portion 117, but have not dropped into the circumferential groove 121.

It now is possible to withdraw the plunger 102 and fill a fluid cavity 164 with liquid from the vial 163, as shown in FIG. 11. Normally retraction continues until the piston 101 abuts the end surfaces 144 and 147 of the arms 141 and 142, respectively or the desired dosage is transferred to the syringe. When the plunger 102 is in this position, the collar section 136 still overlies the circumferential groove 121 to prevent anyone from tampering with it to defeat the one-use function. Prior to the administration of the dose, the plunger 102 typically is advanced a short distance to remove air bubbles.

Figure 12:
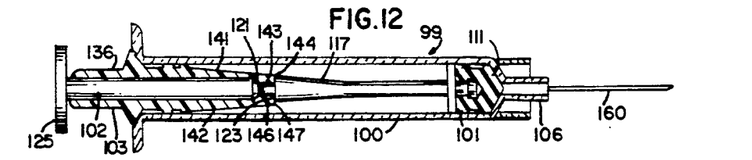
FIG. 12 is a view of the syringe shown in FIG. 9 with the plunger fully advanced to the locking position after use wherein the insert depicted in FIGS. 7A through 7D locks the plunger against further motion.

During the subcutaneous administration of liquid from the syringe 99, pressure applied to the pad 125 again advances the plunger 102 and piston 101 toward the port end 106 thereby to inject fluid through the hypodermic needle 160 into the patient. During this step, the plunger 102 advances until the piston 101 contacts the port end 106. Just before reaching that position, as shown in FIG. 12, the piston 101 and plunger again reach the position shown in FIG. 10. As previously described, the flared stem portion 117 cams the followers 143 and 146 and their respective arms 141 and 142 radially outward at this position. This deflection produces internal restoring forces in the arms 141 and 142. When the plunger 102 and piston 101 move to the position in FIG. 12, the circumferential groove 121 aligns with the radial projections or followers 143 and 146, so the arms 141 and 142 snap, with an audible click, toward the axis 105 thereby to lock the followers 143 and 146 in the circumferential groove 121. Locking occurs because there is interference and overlap between the ends 144 and 147 of the arms 141 and 142 and the radial surface 123 that defines the groove 121. It is not possible to withdraw the plunger 102 from the barrel 100, so the syringe 99 can not be used again.

Further, it is not possible to tamper with the first and second locking means without destroying the syringe 99. The bands 131, 132 and 133 shown in FIGS. 7A, 7B and 8 produce sufficient friction with the barrel 100 to prevent any removal of the insert 103 without destroying the syringe 99. The holding capability of the bands 131, 132 and 133 can be further enhanced by the use of various adhesives, ultrasonic welding or other techniques to bond the insert 103 and the barrel 100.

Thus in accordance with this invention, the embodiment of the syringe 99 shown in FIGS. 6 through 12 comprises a cylindrical barrel 100 that has a passage 104 lying along a longitudinal axis 105 between a port end 106 and a remote end 108 of the barrel 100. The port end 106 is adapted to receive the hypodermic needle 160 for transferring fluid to and from the syringe 99. A piston 101 slides axially in the barrel 100 for defining a fluid cavity 164 bounded by the port end 106 of the barrel 100 and the piston 101; as apparent, the volume of the cavity 164 varies with the axial position of the piston 100.

In this particular embodiment the plunger 102 moves the piston 101 along the longitudinal axis 105 to a locking position at the port end 106 of the barrel means and to other positions displaced from the locking position wherein the piston 101 is displaced from the port end 106. The plunger 102 includes a circumferential groove 121 with a radial surface 123 that defines a locking means formed with the plunger 102.

The insert 103 is affixed to and partially disposed in the barrel 100 in a cavity that is remote from the fluid cavity 164. The barrel is coextensive with at least a portion of the plunger 102 and has second locking means int he forms of radially acting, inwardly directed followers 143 and 146 at the ends of bifurcated arms 141 and 142. The followers 143 and 146 rise over the surfaces of the lunger 102 including the surfaces of the cylindrical and flared stem portions 116 and 117 until the plunger 101 reaches the locking position whereupon the arms 141 and 142 snap the followers 143 and 146 into the circumferential groove 121 and block any further motion of the plunger 102.

Figure 7C:
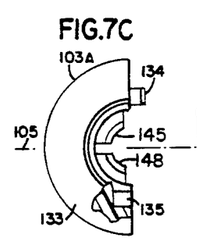
Figure 7D:
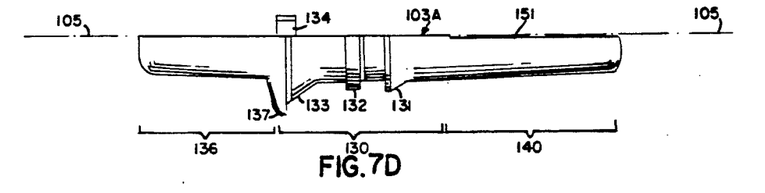
Figure 8:
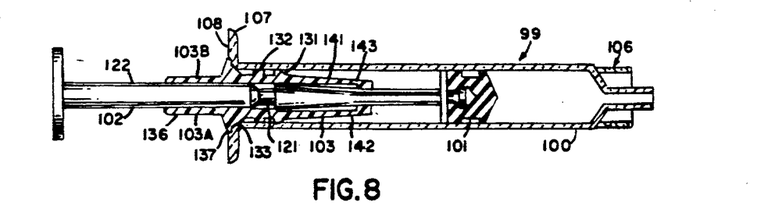
FIG. 8 is a cross section of an assembled syringe using the components depicted in FIGS. 6 and 7A through 7D.
Figure 13:
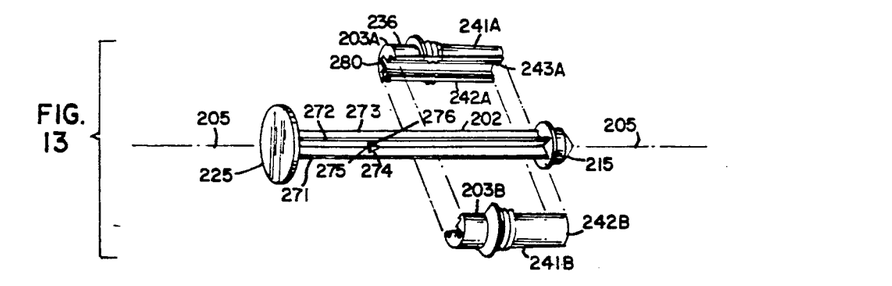
FIG. 13 is a perspective view of an another insert and plunger that is useful in an alterative embodiment of this invention.

FIG. 13 is an exploded perspective view that illustrates the construction of an insert adapted from the construction shown in FIGS. 6 through 8 for large volume syringes that utilize a plunger 202 with a cruciform cross-section. The plunger 202 has a pad 225 at one end and a piston-connecting structure 215 at the other end. In this particular embodiment the interconnecting structure comprises four longitudinally extending orthogonal ribs that radiate from a central portion that lies on the axis 205. Only ribs 271, 272, and 273 are shown; the fourth rib is hidden from view in FIG. 13.

In this embodiment the first locking means associated with the plunger 202 comprises a filet 274 at each intersection of contiguous pairs of the orthogonal ribs. Each filet 274 has a radial surface 275 in a plane perpendicular to the axis 205 and a ramped surface 276 that slopes simultaneously toward the axis 205 and the port end 206. Each filet 274 is displaced axially with respect to the interconnecting structure 215 by a distance that corresponds to the position of the plunger 202 when the piston 201, shown in FIG. 14, is at the port end 206 of the barrel 200.

As shown more particularly in FIG. 13, insert components 203A and 203B have the same general configuration as the inserts 103A and 103B shown in FIGS. 6 through 8. The component 203A has arms 241A and 242A while the component 203B has arms 241B and 242B. Referring to component 203A, the spacing between adjacent arms 241A and 241B corresponds to the thickness of the ribs 271 through 273, so the ribs slide axially between the arms 241A and 241B. The arms 241A and 241B occupy distinct quadrants when viewed in cross section and terminate, at their free ends, with radially acting, inwardly direction projections that act as followers. A follower 243A at the end of the arm 201A has a triangular cross-section to conform to and fit in the area between adjacent ribs 272 and 273.

Figure 14:
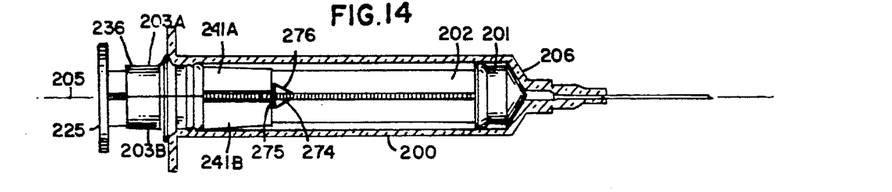
FIG. 14 is a view of a syringe utilizing the insert and plunger of FIG. 13 when the plunger is fully advanced and locked.

As the plunger 202 moves toward the locking position shown in FIG. 14, the ramped surfaces 276 cam the arms 241A and 242B radially outward. When the plunger 202 reaches the locking position as shown in FIG. 14, the restoring forces that build during the deflection act through the arms, such as arms 241A and 241B, to snap the followers, such as follower 243A, over the filets 274 against the radial surfaces 275 to prevent further plunger motion.

The insert components 203A and 203B additionally include transverse end portions 280 that close a collar section 236. The end portions 280 are relieved to provide, when assembled, a cruciform opening that conforms to the cross-section defined by the radially extending orthogonal ribs, such as ribs 271 through 273.

This enables the end portions 280 to guide and support the plunger 202 during its axial motion.

With the embodiment of FIG. 14, the locking means formed by the filets 274 on the plunger 202 may be accessible when the plunger 202 is fully retracted. In such constructions the openings in the end portions 280 can be formed to accommodate the filets 274. Although such a modification does provide a potential for tampering with the locking mechanism, this syringe is still acceptable because it locks the plunger and prevents any use beyond a first, legitimate use. Alternatively, the collar 236 can be extended so the axial distance inside the insert 203 exceeds the axial displacement of the plunger 202 with a concomitant increase in the lengths of the plunger 202 and the syringe.

Figure 15:
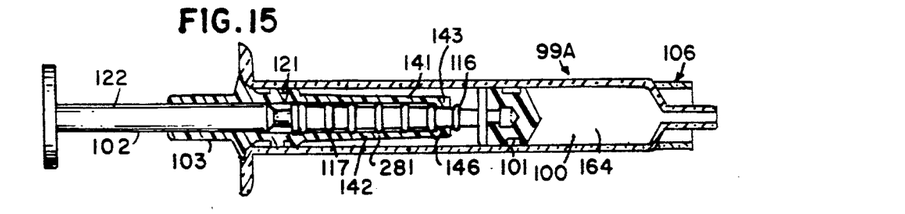
FIG. 15 depicts an alternative embodiment of a syringe such as shown in FIG. 9 with an added position detent feature.

FIG. 15 depicts a syringe 99A that is a modification of the syringe 99 shown in FIG. 8. Like numerals refer to like elements in both figures. This modification enables an individual to gauge the amount of medication that has been administered. Specifically, the syringe 99A produces "clicks" as incremental dosage amounts are administered. For example, each "click" might indicate the administration of 0.1 cc. The syringe 99A, like the syringe 99, has a barrel 100, for supporting a hypodermic needle at a port end 106. Fluid is drawn into and forced from a cavity 164 by a piston 101 mounted at the end of a plunger 102. An insert 103 provides the locking action described with respect to FIGS. 6 through 12 when followers 143 and 146 snap into a circumferential groove 121 formed intermediate the flared and second stem portions 117 and 122 respectively.

Still referring to FIG. 15 in this particular embodiment, a series of equally spaced circumferential rings 281 along the lengths of the first cylindrical stem portion 116 and flared stem portion 117 provide the "clicking". These rings 281 can have any of a wide variety of shapes that will coact with the followers 143 and 146. As the followers 143 and 146 at the ends of the arms 141 and 142 wipe across the surface of the stem portions 116 and 117, the followers 143 and 146 perform a detent function by dropping the space between adjacent rings 281 in succession with a "click" sound. So long as each ring 281 is rounded and has little elevation, the followers 143 and 146 do not block axial motion of the plunger 102 while it moves through positions remote from the locking position. It is easy to move the plunger with this detent action and detent action provides a smooth feedback to the individual administering medication.

As apparent, a syringe constructed in accordance with this invention provides this added function without adding components to the syringe. Moreover, the detent function can be achieved by substituting a groove for each ring and providing a follower on the end of each follower that will drop into the grooves as they pass in succession.

Figure 16:
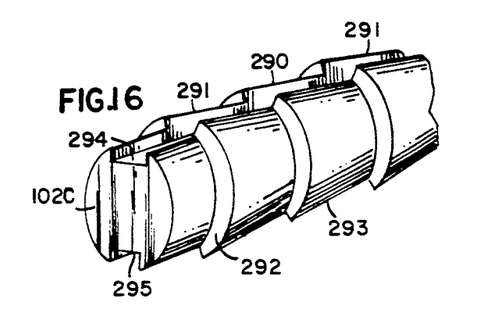
FIG. 16 is a perspective view of another plunger construction useful in this invention for metering doses administered by the syringe.
Figure 17:
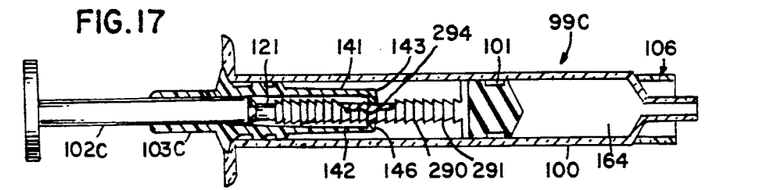
FIG. 17 illustrates a syringe with the plunger of FIG. 16 oriented to allow the plunger to be withdrawn.
Figure 18:
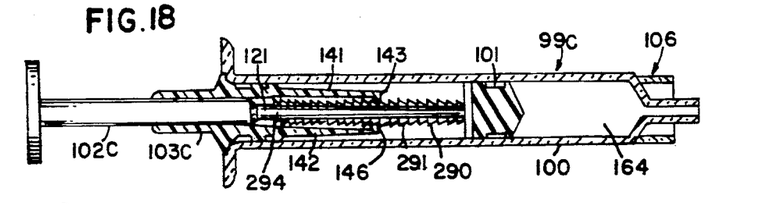
FIG. 18 depicts the plunger in a position for being advanced during which metering can occur.

FIGS. 16 through 18 disclose another embodiment of the syringe 99 in FIG. 6. This syringe, identified by reference number 99C in FIGS. 17 and 18, allows the administration of metered doses in bolus applications in which backflow into the syringe is not desired. That is, once a dose, or portion thereof, is administered, the syringe 99C prevents any fluid reentering from the syringe 99C. For example, a syringe 99C can be connected, through conventional Luer Lock fittings to a intravenous line. After a dose, corresponding to less than the quantity in the syringe 99C, is administered, the syringe 99C can be left attached to the intravenous line because the syringe 99C prevents any liquid from the intravenous line from backing into the cavity 164.

As shown in detail in FIGS. 16 through 18, a modified plunger 102C is characterized by a single cylindrical stem portion 290 between the piston 101 and the circumferential groove 121. This stem portion 290 has a series of outwardly directed teeth 291 along its surface. Each tooth 291 has a transverse radial surface 292 and a conical surface 293 that tapers toward the port end 106, i.e., towards the piston 101. In addition, the plunger 102C has two axially extending smooth slide surfaces formed a diametrically opposed locations. As shown in FIG. 16, one surface 294 extends axially along the top of the plunger 102C while a second surface 295 is positioned at the bottom. The plane of each surface 294 and 295 will normally be coextensive with the intersections the conical surfaces 293 and the radial surfaces 292 of the teeth 291.

A second modification is made to the insert . In FIGS. 17 and 18, the insert 103C has only two arms 141 and 142, one on each insert half. The other two arms are removed from the insert 103. As a result, the arms 141 and 142 are diametrically opposed.

During use, the plunger 102C can be rotated in the barrel 100 angularly between the positions in FIGS. 17 and 18 In the former figure, the arms 141 and 142 position their respective followers 143 and 146 over the smooth planar surfaces 294 and 295. Thus, it is possible to move the plunger 102C axially over the same range of motion as shown in FIG. 8 so it is simple to fill the cavity 164 of the syringe 99C. During administration, the plunger 102C is rotated to the position shown in FIG. 18. Now the smooth surfaces 294 and 295 are rotated 90 away from the followers 143 and 146, and the followers 143 and 146 ride over the teeth 291. As the plunger 102C moves toward the port end 106, the followers 143 and 146 ride over successive teeth. During this plunger motion, the insert 103C provides audible "clicks" similar to the "clicks" provided by the syringe 99A in FIG. 15. When the followers 143 and 146 engage a tooth, however, they block any attempt to move the plunger 102C away from the port end 106. This blocking action prevents an inadvertent withdrawal of the plunger 102C or the reverse flow of fluids through the port end 106 from an external source. If the individual wishes to withdraw the plunger 102C, it is merely necessary to rotate the plunger 102C until the smooth surfaces 294 and 295 align under the followers 143 and 146.

Again; the syringe 99C provides these added functions without adding components to the syringe. Moreover, the functions are provided in addition to the primary locking function. As apparent, when the plunger 102C reaches the port end 106, in any angular orientation of the plunger 102C, the followers 143 and 146 engage the circumferential groove 121 to block any further use of the syringe 99C.

Figure 19:
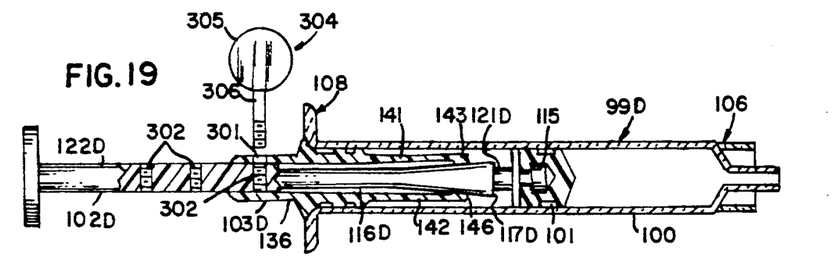
FIG. 19 depicts another syringe that is adapted for catheter applications and that includes a plunger locking mechanism.

FIG. 19 depicts yet another embodiment of a syringe constructed in accordance with this invention that is adapted for withdrawing, rather than administering, fluids. In some modalities it is desirable to inflate and deflate a catheter in succession. With conventional syringes, a separate valve controls fluid flow independently of the syringe. Normally the syringe is discarded after deflation. The syringe 99D in FIG. 19 is adapted for withdrawing fluids, as during the deflation of a catheter, and for providing the function of an independent valve structure.

The syringe 99C in FIG. 19 has a barrel 100 with a port end 106, a remote end 108 and a piston 101 that slides axially within the barrel 100 that is particularly useful in catheter applications. An insert 103D, generally having the same general construction as the insert 103 in FIG. 8, includes a single aperture 301 through the collar section 136. Alternatively the aperture 301 may align with another aperture through the collar section 136 diametrically across from the aperture 301. The plunger 102D is also modified by adding one or more axially spaced, threaded holes 302 formed partially or completely through a cylindrical stem portion 122D of the plunger 102D. When the aperture 301 aligns with one of the apertures 302, a detachable threaded locking device 304 with a handle portion 305 and threaded screw portion 306 can be secured in the plunger 102D through the collar 136 thereby to lock the position of the plunger 102D. Thus, after inflating a catheter it is merely necessary to insert the locking device 304 to maintain pressure in the catheter.

As disclosed later, there are various modifications for this locking scheme. For example, the use of aligned apertures 301 in the collar portion 136 and through holes in place of the threaded holes 302 allow the use of locking devices in which extended smooth pins or clips are substituted for the threaded screw portion 306 shown in FIG. 19. As another example, circumferential grooves can replace the threaded holes 302 in the plunger 102D and diametrically opposed tangential slots can replace the apertures 301. With this construction a bifurcated spring clip can slide over the collar portion 136 and engage a groove through the tangential slots. In another embodiment friction locking of the plunger 102D at any position can be achieved by merely replacing the aperture 301 with a threaded aperture and, optionally, eliminating the apertures 302. The locking device 304 would then abut the surface of the plunger 102D at any position. Still other modifications can be adapted for implementing this locking function.

The plunger 102D is also modified to adapt its use in a syringe that is discarded after the plunger 102D is withdrawn. As shown in FIG. 19, the plunger 102C has a connecting structure 115 for engaging the piston 101. However, in this embodiment, a circumferential groove 121D is formed immediately adjacent the structure 115. The remainder of the plunger 102D comprises, in axial alignment, a flared end portion 117D, a reduced diameter cylindrical stem portion 116D and the apertured second cylindrical stem portion 122D. As will be apparent, the plunger 102D reaches the locking position when it is fully withdrawn from the port end 106. At this position, the arms 141 and 142 snap the followers 143 and 146 into the groove 121D so the syringe 99D can not be used again.

Figure 20:
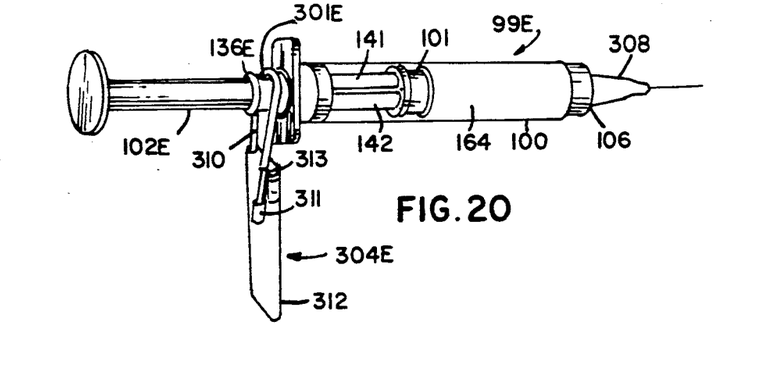
FIG. 20 is an embodiment of a syringe as shown in FIG. 19 with an alternative plunger locking mechanism for other applications.

FIG. 20 discloses a syringe 99E that is particularly adapted for blood gas and other aspiration procedures. The syringe 99E has the same general form as the syringe 99 in FIG. 8. That is, the syringe 99E has a barrel 100 with a support for a hypodermic needle 308 or the like at a port end 106. A piston 101 is adapted for forcing medication into and from the cavity 164. During an aspiration the plunger 102E initially will be withdrawn to the position shown in FIG. 20. Then a locking device 304E can be inserted through aligned apertures 301E in the collar 136E and an aperture in the plunger 102E.

For aspirations, the locking device 304E comprises a cable 310 with a free end 311 that loops through the apertures. The other end of the cable 310 is integral with a tag 312 for enabling sample labeling. The tag 312 also will have a one-use clamp 313 that is affixed to the free end 311 to seal the cable 310 and tag 312 together. The syringe 99E then can be safely transported to a laboratory where the cable 310 is cut and the syringe 99E emptied. When this occurs, the plunger 102E is pushed toward the port end 106 until followers on arms 141 and 142 engage a circumferential groove (not shown) that is equivalent to the groove 121 in FIG. 6. This prevents further use of the syringe This concept may also be used when prefilling syringes in a general filling area. In such applications the tag 312 could contain information identifying the patient and the medications.

Figure 21:
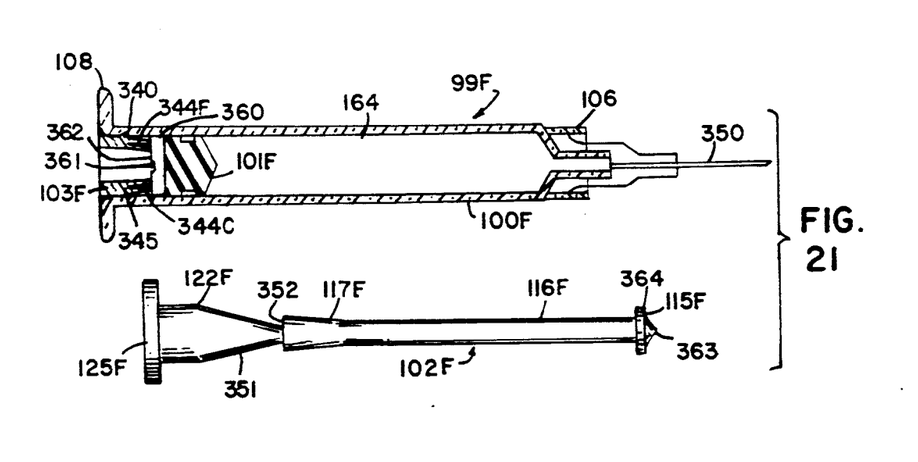
FIG. 21 is a view of a tamper evident prefilled glass syringe adapted for shipment with a separated plunger.
Figure 22:
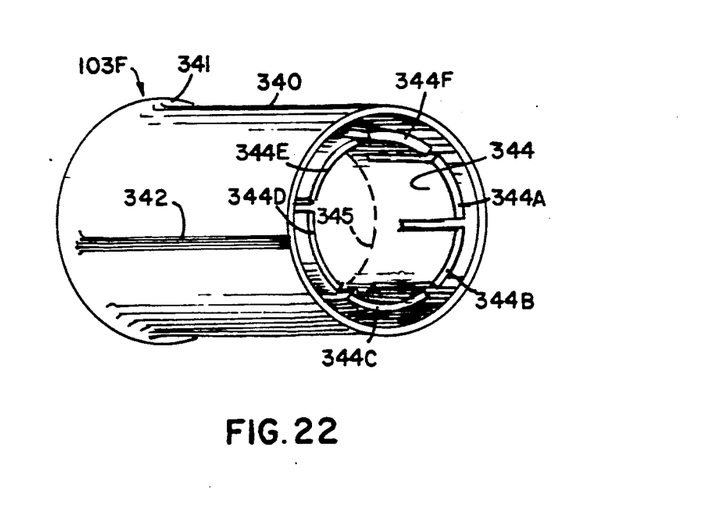
FIG. 22 is an enlarged perspective view of an insert that is adapted for use in the syringe depicted in FIG. 21.

FIGS. 21 and 22 discloses a pre-filled glass syringe 99F adapted for incorporating this invention. The syringe 99F comprises a glass barrel 100F with a hypodermic needle 350 affixed to the port end 106. The syringe 99F also comprises a piston 101F and a modified insert 103F that is shorter axially than the insert 103 in FIG. 6. The exterior surface of the insert 103F may also be modified to accommodate any internal structures of the barrel 100E at the remote end 108.

As shown in detail in FIG. 22, the insert 103F has an outer cylindrical shell 340 with a flared end section 341. The outer dimensions of the shell 340 enable it to be held firmly in place in the remote end 108 of the glass barrel 100F as shown in FIG. 21. Longitudinal grooves 342 can assist in holding the shell 340 in place. Chemically stable adhesives can also be used.

An inner conical shell 344 is formed of a plurality of spaced, longitudinally extending segments or arms 344A through 344F that extend from a midpoint, shown by a dashed circumferential line 345. The end of each segment or arm thereby is free to pivot radially.

The syringe 99F in FIG. 21 also has a modified plunger 102F in which a tapered section 351 replaces the cylindrical portion that forms the circumferential groove 121 in FIG. 6. More specifically, the plunger 102F has a piston engaging structure 115F, a first cylindrical stem portion 116F, a flared stem portion 117F, the tapered portion 351, a second cylindrical stem portion 122F and a thumb pad 125F.

In the embodiment of FIG. 21, the piston 101F also is modified. It has formed therewith, by any of a variety of means, a metallic or hard washer 360 or the like to provide a center hole or depression 361 and a hard bearing surface 362. Moreover, the piston engaging section 115F can be adapted to interact with the piston 101F in either of two ways. As when in FIG. 21, the piston engaging section has conical tip portion 363 that centers on the depression 361 formed in the washer 360. A flange 364 bears against the washer surface 362 thereby to transfer force from the plunger 102F across the face of the piston 101F. Alternatively, the piston engaging end 115F can comprise a threaded shank that screws into a threaded insert in the piston 101F. The applications for these diverse piston structures will be described later.

The manufacturer of a prefilled glass syringe 99F assembles a barrel 100F, piston 101F and insert 103F and fills the cavity 164 for shipment with a separate plunger 102F. When it is time to use the syringe 99F, the plunger 102F is inserted into the glass barrel 100F and toward the piston 101F. As the plunger 102F advances, it pushes the cylindrical stem portion 116F and then the flared stem portion 117F past the arms 344A through 344F. The flared stem portion 117F drives the arms 344A through 344F apart and thereby to generate internal restoring forces. When the piston 101F reaches the port end 106, the restoring forces in the arms 344A through 344F snap the followers, constituted by either radial projections at the free ends of or, as shown in FIGS. 21 and 22 merely the free ends of the arms 344A through 344F, against the flared locking portion 351 and into abutment with a radial surface 352 that defines a boundary between the flared locking portion 351 and the flared stem portion 117F. This abutment prevents the removal of the plunger 102F after use. Thus no, one can refill the syringe 99F because the plunger 102F blocks any motion of the piston 101.

The insert 103F and a plunger 102F as shown in FIG. 21 provide another function if the flange 364 has a dimension that is greater than the dimension of the opening defined by the arms 344A through 344F. As soon as the flange 364 passes the end of the insert 103F, it is locked in the syringe 99F. Thus, anyone receiving a syringe 99F with an inserted plunger 102F is on notice that tampering may have occurred.

The connection between the piston engaging end 115F and the piston 101F is a one-way connection. It is not possible to draw the piston back to the remote end 108. Any corresponding motion by the plunger 102F merely displaces it from the piston 101F.

If a threaded shank and tapped insert replace the conical tip 363 and washer 360, it is possible to withdraw the piston. In such an embodiment, the presence of the plunger 102F in the barrel does not necessarily indicate tampering. Thus, a plunger 102F with a threaded shank may also eliminate the flange 364. However, even with these modifications, all embodiments continue to provide the primary locking function that prevents reuse of the syringe 99F.

In summary, each of the syringe embodiments disclosed in FIGS. 1 through 22 have certain common functional and structural characteristics. They each include a barrel, a piston, a plunger and an insert for preventing anyone from reusing the syringe. Each insert has plural arms that extend from a central body portion toward a port end of the syringe. Followers at the free ends of the arms engage a locking surface on the plunger when the plunger and piston reach a locking position defined as the position of the piston at the port end of the syringe or displace from the port end.

It will be apparent, however, that a number of variations of the basic concepts disclosed in the several syringe embodiments can be implemented with the attainment of all or some of the objects and advantages of this invention. For example, different plunger constructions adapt syringes for different end uses. The plungers may have a generally cylindrical or a cruciform cross section; they may have a smooth surface, a detented surface or a surface with alternate smooth and toothed portions. The inserts may have arms of different lengths that terminate with radially acting, inwardly directed followers that may comprise merely the free end of an arm or a discrete projection from the arm. Different syringes may include diverse end configurations to accommodate different attachment structures, such as hypodermic needles. A given syringe may use a plunger with a cylindrical, a cruciform or other cross-sections Generally these syringes will be constructed from moldable plastic or glass materials and by processes that are well known in the art. However, this invention is not limited to such materials and processes. Therefore, it is the object of the appended claims to cover all such variations and modifications as come within the true spirit and scope of this invention.

What is claimed as new and desired to be secured by Letters Patent of the United States is:

1. A syringe comprising:
   A. cylindrical barrel means having passage means extending along a longitudinal axis between a port end and a remote end, means at said port end for enabling the transfer of fluid to and from said syringe,
   B. piston means for sliding axially in said barrel means, said cylindrical barrel means and said piston means forming a fluid cavity bounded by said port end and said piston means whereby the volume of said fluid cavity varies with the axial position of said piston means,
   C. plunger means for moving said piston means along the longitudinal axis to a locking position at one end of said fluid cavity and to other positions displaced from said locking position, said plunger means having first locking means formed therewith, and
   D. insert means affixed to and at least partially disposed in said barrel means at said remote end and coextensively with a portion of said plunger means, said insert means having second locking means in said barrel means for riding over said plunger means during axial motion of said plunger means in said other positions and for engaging said first locking means when said plunger means moves to said locking position thereby to block said plunger means from further axial motion.

2. A syringe as recited in claim 1 wherein said plunger means comprises longitudinally extending orthogonal ribs joined at a central portion along the longitudinal axis, said insert means having an end structure external to said barrel means with an opening that conforms to the cross-section of said plunger means for supporting said plunger means during axial movement, and wherein said first locking means comprises a radial surface extending from said central portion for engaging said second locking means when said piston means reaches said locking position.

3. A syringe as recited in claim 2 wherein said insert means has a central body means for engaging said barrel means and said second locking means comprises a flexible arm means extending toward said port end and terminating at a free end thereof with a radial projection extending toward the longitudinal axis, said first locking means having a cam surface extending from said radial surface toward the port end for engaging said radial projection thereby to deflect said flexible arm outwardly as said plunger means moves to said locking position.

4. A syringe as recited in claim 3 wherein said insert means has a longitudinal dimension that corresponds to the axial displacement of said plunger means whereby said first locking means is inaccessible in all positions of said plunger means.

5. A syringe as recited in claim 3 wherein said insert means has a longitudinal dimension that is less than the axial displacement of said plunger means, said first locking means initially lying outside said insert means, said insert means end structure enabling said cam surface to pass said end structure as said plunger means moves toward said locking position.

6. A syringe as recited in claim 1 wherein said piston means and said plunger end of said barrel means define a second cavity in said barrel means, said portions of said insert means disposed in said barrel means being located in said second cavity.

7. A syringe as recited in claim 6 wherein said insert means has a central body means for positioning said insert means in said second cavity and said second locking means comprises at least one flexible arm extending toward said port end of said barrel means and terminating at a free end thereof with a radially acting, inwardly directed follower, said free end defining a stop for limiting motion of said piston means toward said remote end and defining the maximum volume of said fluid cavity.

8. A syringe as recited in claim 6 wherein said barrel means has a cylindrical passage means and wherein said insert means has a cylindrical body means for positioning said insert means in said second cavity and said second locking means comprises a plurality of flexible arms spaced radially about said central body section and extending toward said port end, each said arm terminating in a radially acting, inwardly directed follower, said first locking means comprising a circumferential groove in said plunger means for receiving said followers when said plunger means is at said locking position.

9. A syringe as recited in claim 8 wherein said plunger means is at said locking position when said piston means is at said port end of said barrel means.

10. A syringe as recited in claim 9 wherein said plunger means comprises, in axial alignment, means for engaging said piston means, a first cylindrical stem portion, a flared stem portion, a reduced diameter portion for defining said circumferential groove, a second cylindrical stem portion, and pad means for moving said plunger means, said circumferential groove being displaced from said piston means by a distance corresponding to the distance between said piston means and said radial followers of said insert means when said piston means is at said locked position.

11. A syringe as recited in claim 10 wherein said cylindrical and flared stem portions of said plunger means have equally and axially spaced circumferential detents formed therein, said followers riding in said detents as said plunger means moves axially to provide an audible indication of equal changes in the volume of said fluid cavity.

12. A syringe as recited in claim 10 wherein said insert means includes collar means concentric with the longitudinal axis and extending externally to said remote end of said barrel means, said collar means having an aperture formed therein and wherein said plunger means has an aperture formed therethrough for alignment with said aperture in said collar means at a predetermined position of said plunger means, said syringe additionally comprising third locking means for engaging said collar means and said plunger means when said apertures align thereby to block motion of said plunger means with respect to said syringe.

13. A syringe as recited in claim 12 wherein said third locking means is detachable from said syringe.

14. A syringe as recited in claim 13 wherein at least one of said apertures in said collar and plunger means is threaded and said locking mechanism comprises a threaded key structure for engaging the threaded portion in one said aperture.

15. A syringe as recited in claim 13 wherein said third locking means comprises a flexible member adapted to be inserted through said aligned apertures and means associated with said flexible means for closing a loop thereof to prevent unauthorized removal of said flexible means.

16. A syringe as recited in claim 13 wherein said plunger means has a plurality of axially spaced apertures therethrough for alignment with said apertures in said collar means at different axial positions of said plunger means.

17. A syringe as recited in claim 12 wherein said syringe is adapted for being filled with a fluid without said plunger means being attached to said piston means, said insert means terminating at said remote end of said barrel means for directing a said plunger means to engagement with said piston means thereby to advance said piston means to administer the fluid, said plunger means including said first locking means for engagement by said second locking means insert means when said piston reaches the locking position.

18. A syringe as recited in claim 9 wherein said plunger means comprises, in axial alignment, means for engaging said piston means, a first cylindrical stem portion, a reduced diameter portion for defining said circumferential groove, a second cylindrical stem portion, and pad means for moving said plunger means, said circumferential groove being displaced from said piston means by a distance corresponding to the distance between the said piston means and said followers of said insert means when said piston means is at said locked position, said first cylindrical stem portion having angularly displaced smooth and toothed surface sections extending along the length thereof and said plunger means being rotatable about its axis to align said smooth surface sections with said followers in one angular position to enable axial motion of said plunger means in both directions and to align said toothed surface sections with said followers in another angular position whereby said second locking means enables motion of said plunger means toward said locking position and blocks motion away from said locking position.

19. A syringe as recited in claim 8 wherein said plunger means is at said locking position when said piston means is displaced from said port end of said barrel means and abuts said insert means.

20. A syringe as recited in claim 19 wherein said plunger means comprises, in axial alignment, means for engaging said piston means, a reduced diameter portion for defining said circumferential groove, a flared stem portion, a cylindrical stem portion and pad means for moving said plunger means, said followers of said insert means engaging said plunger means at said circumferential groove when said piston means is at said locked position at said insert means.

21. A syringe as recited in claim 20 wherein said insert means includes collar means concentric with the longitudinal axis and extending externally to said remote end of said barrel means, said collar means having an aperture formed therein and wherein said plunger means has an aperture formed therethrough for alignment with said aperture in said collar means at a predetermined position of said plunger means, said syringe additionally comprising third locking means for engaging said collar means and said plunger means when said apertures align thereby to block motion of said plunger means with respect to said syringe.

22. A syringe as recited in claim 21 wherein said third locking means is detachable from said syringe.

23. A syringe as recited in claim 21 wherein at least one of said apertures in said collar and plunger means is threaded and said locking mechanism comprises a threaded key structure for engaging the threaded portion in one said aperture.

24. A syringe as recited in claim 21 wherein said third locking means comprises a flexible member adapted to be inserted through said aligned apertures and means associated with said flexible means for closing a loop thereof to prevent unauthorized removal of said flexible means.

25. A syringe comprising:
   A. cylindrical barrel means having passage means extending along a longitudinal axis between a port end and a remote end, means at said port end for enabling the transfer of fluid to and from said syringe,
   B. piston means for sliding axially in said barrel means, said cylindrical barrel means and said piston means forming a fluid cavity bounded by said port end and said piston means whereby the volume of said fluid cavity varies with the axial position of said piston means,
   C. plunger means for moving said piston means along the longitudinal axis to a locking position when said piston means is adjacent said port end of said fluid cavity and to other positions displaced from said locking position, said plunger means having a circumferential groove that is axially displaced from said piston means, and
   D. insert means affixed to and at least partially disposed in said barrel means at said remote end and coextensively with a portion of said plunger means, said insert means including a cylindrical body means for positioning said insert means in said second cavity and a plurality of flexible arms spaced radially about said central body section and extending toward said port end, each said arm terminating in a radially acting, inwardly directed follower, said followers locking in said circumferential groove when said plunger means is at said locking position thereby to block said plunger means from further axial motion.

26. A syringe as recited in claim 25 wherein said plunger means comprises, in axial alignment, means for engaging said piston means, a first cylindrical stem portion, a flared stem portion, said circumferential groove, a second cylindrical stem portion, and pad means for moving said plunger means, said circumferential groove being displaced from said piston means by a distance corresponding to the distance between the said piston means and said followers of said insert means when said piston means is at said locked position.

27. A syringe as recited in claim 25 wherein said insert means includes collar means concentric with the longitudinal axis and extending externally to said remote end of said barrel means with an aperture formed therein and wherein said plunger means has an aperture formed therethrough for alignment with said aperture in said collar means at a predetermined position of said plunger means, said syringe additionally comprising third locking means for detachably engaging said collar means and said plunger means when said apertures align thereby to block motion of said plunger means with respect to said syringe.

28. A syringe as recited in claim 27 wherein said insert means comprises two complementary semicylindrical components, each component having:
   i. a semicylindrical body means extending along the longitudinal axis for positioning said insert means in said second cavity,
   ii. a semicylindrical collar extension concentric with the longitudinal axis and extending externally to said remote end of said barrel means for forming said collar means,
   iii. a pair of flexible arms spaced radially about said central body section and extending from said body means toward said port end, each said arm terminating in a said radially acting, inwardly directed follower, and
   iv. locating means for aligning a pair of said components to form said insert.

29. A syringe comprising:
   A. cylindrical barrel means having passage means extending along a longitudinal axis between a port end and a remote end, means at said port end for enabling the transfer of fluid to and from said syringe,
   B. piston means for sliding axially in said barrel means, said cylindrical barrel means and said piston means forming a fluid cavity bounded by said port end and said piston means whereby the volume of said fluid cavity varies with the axial position of said piston means,
   C. plunger means for moving said piston means along the longitudinal axis to a locking position when said piston means is adjacent said port end of said fluid cavity and to other positions displaced from said locking position, said plunger means having a circumferential groove that is axially displaced from said piston means and axially spaced detent grooves intermediate said piston means and said circumferential groove, and
   D. insert means affixed to and at least partially disposed in said barrel means at said remote end and coextensively with a portion of said plunger means, said insert means including a cylindrical body means for positioning said insert means in said second cavity and a plurality of flexible arms spaced radially about said central body section and extending toward said port end, each said arm terminating in a radially acting, inwardly directed follower, said followers providing a detent action as said detent grooves pass and locking in said circumferential groove when said plunger means is at said locking position thereby to block said plunger means from further axial motion.

30. A syringe as recited in claim 29 wherein said plunger means comprises, in axial alignment, means for engaging said piston means, a first cylindrical stem portion, a flared stem portion, said circumferential groove, a second cylindrical stem portion, and pad means for moving said plunger means, said circumferential groove being displaced from said piston means by a distance corresponding to the distance between the said piston means and said followers of said insert means when said piston means is at said locked position and said detent grooves being formed along the length of said first cylindrical and flared stem portions.

31. A syringe as recited in claim 30 wherein said insert means includes collar means concentric with the longitudinal axis and extending externally to said remote end of said barrel means, said collar means covering said circumferential groove when said plunger means is fully displaced toward said remote end.

32. A syringe as recited in claim 31 wherein said insert means comprises two complementary semicylindrical components, each component having:

i. a semicylindrical body means extending along the longitudinal axis for positioning said insert means in said second cavity, ii. a semicylindrical collar extension concentric with the longitudinal axis and extending externally to said remote end of said barrel means for forming said collar means, iii. a pair of flexible arms spaced radially about said central body section and extending from said body means toward said port end, each said arm terminating in a said radially acting, inwardly directed follower, and iv. locating means for aligning a pair of said components to form said insert.

33. A syringe comprising:

A. cylindrical barrel means having passage means extending along a longitudinal axis between a port end and a remote end, means at said port end for enabling the transfer of fluid to and from said syringe, B. piston means for sliding axially in said barrel means, said cylindrical barrel means and said piston means forming a fluid cavity bounded by said port end and said piston means whereby the volume of said fluid cavity varies with the axial position of said piston means, C. plunger means for moving said piston means along the longitudinal axis to a locking position when said piston means is adjacent said port end of said fluid cavity and to other positions displaced from said locking position, said plunger means having a circumferential groove that is axially displaced from said piston means and, intermediate said piston means and said circumferential groove, first and second sets of diametrically opposed radially outwardly extending teeth and axially extending smooth surfaces between said sets of teeth, said plunger means being rotatable about the longitudinal axis in said barrel means, and D. insert means affixed to and at least partially disposed in said barrel means at said remote end and coextensively with a portion of said plunger means, said insert means including a cylindrical body means for positioning said insert means in said second cavity and a pair of diametrically opposed flexible arms extending toward said port end, each said arm terminating in a radially acting, inwardly directed follower, said followers locking in said circumferential groove when said plunger means is at said locking position thereby to block said plunger means from further axial motion, said followers sliding over said smooth surface for one angular position of said plunger means and providing one-way blocking of said plunger means by interacting with said teeth in another angular position of said plunger means.

34. A syringe as recited in claim 33 wherein said plunger means comprises, in axial alignment, means for engaging said piston means, a first cylindrical stem portion, said circumferential groove, a second cylindrical stem portion, and pad means for moving said plunger means, said circumferential groove being displaced from said piston means by a distance corresponding to the distance between the said piston means and said followers of said insert means when said piston means is at said locked position and said teeth and smooth surfaces being formed along the length of said first cylindrical stem portion.

35. A syringe as recited in claim 34 wherein said insert means includes collar means concentric with the longitudinal axis and extending externally to said remote end of said barrel means, said collar means covering said circumferential groove when said plunger means is fully displaced toward said remote end.

36. A syringe as recited in claim 35 wherein said insert means comprises two complementary semicylindrical components, each component having:

i. a semicylindrical body means extending along the longitudinal axis for positioning said insert means in said second cavity, ii. a semicylindrical collar extension concentric with the longitudinal axis and extending externally to said remote end of said barrel means for forming said collar means, iii. a flexible arm extending from said body means toward said port end, said arm terminating in a said radially acting, inwardly directed follower, and iv. locating means for aligning a pair of said components to form said insert.

37. A syringe comprising:

A. cylindrical barrel means having passage means extending along a longitudinal axis between a port end and a remote end, means at said port end for enabling the transfer of fluid to and from said syringe, B. piston means for sliding axially in said barrel means, said cylindrical barrel means and said piston means forming a fluid cavity bounded by said port end and said piston means whereby the volume of said fluid cavity varies with the axial position of said piston means, C. plunger means for moving said piston means along the longitudinal axis to a locking position when said piston means is remote from said port end of said fluid cavity and to other positions displaced from said locking position, said plunger means having a circumferential groove axially adjacent said piston means, and D. insert means affixed to and at least partially disposed in said barrel means at said remote end and coextensively with a portion of said plunger means, said insert means including a cylindrical body means for positioning said insert means in said second cavity and a plurality of flexible arms spaced radially about said central body section and extending toward said port end, each said arm terminating in a radially acting, inwardly directed follower, said followers locking in said circumferential groove when said plunger means is at said locking position thereby to block said plunger means from further axial motion.

38. A syringe as recited in claim 37 wherein said plunger means comprises, in axial alignment, means for engaging said piston means, said circumferential groove, a flared stem portion, a cylindrical stem portion and pad means for moving said plunger means.

39. A syringe as recited in claim 38 wherein said insert means includes collar means concentric with the longitudinal axis and extending externally to said remote end of said barrel means with an aperture formed therein and wherein said plunger means has an aperture formed therethrough for alignment with said aperture in said collar means at a predetermined one of the other positions of said plunger means, said syringe additionally comprising third locking means for detachably engaging said collar means and said plunger means when said apertures align thereby to block motion of said plunger means with respect to said syringe when said plunger means is at said other position.

40. A syringe as recited in claim 39 wherein said insert means comprises two complementary semicylindrical components, each component having:
  i. a semicylindrical body means extending along the longitudinal axis for positioning said insert means in said second cavity,
  ii. a semicylindrical collar extension concentric with the longitudinal axis and extending externally to said remote end of said barrel means for forming said collar means,
  iii. a pair of flexible arms spaced radially about said central body section and extending from said body means toward said port end, each said arm terminating in a said radially acting, inwardly directed follower, and
  iv. locating means for aligning a pair of said components to form said insert.

* * * * *

UNITED STATES PATENT AND TRADEMARK OFFICE
CERTIFICATE OF CORRECTION

PATENT NO. : 5,127,906

DATED : July 7, 1992

INVENTOR(S) : Maurice J. Landry, Jr. and Frederick L. Plouff

It is certified that error appears in the above-identified patent and that said Letters Patent is hereby corrected as shown below:

| | |
|---|---|
| Column 1, line 28 | after "barrel" insert a period -- . -- |
| Column 1, line 28 | after "thereof" insert a period -- . -- |
| Column 2, line 29 | delete "mans" and insert -- means -- |
| Column 3, line 17 | delete "alterative" and insert -- alternative -- |
| Column 5, line 31 | delete "116, a flared" and insert -- 116, and a flared -- |
| Column 5, line 55 | delete "a" and insert -- an -- |
| Column 6, line 15 | after "7D" insert a comma -- , -- |
| Column 8, line 7 | delete "int he" and insert -- in the -- |
| Column 8, line 10 | delete "lunger" and insert -- plunger -- |
| Column 9, line 63 | delete "reentering from" and insert -- from reentering -- |
| Column 10, line 12 | delete "formed a" and insert -- formed at -- |
| Column 10, line 16 and 17 | delete "intersections the conical surfaces" and insert -- intersections of the conical surfaces -- |
| Column 10, line 26 | delete "18 In" and insert -- 18. In -- |
| Column 12, line 10 | delete "syringe This" and insert -- syringe. This -- |
| Column 12, line 51 | after "has" insert -- a -- |
| Column 13, line 1 | delete "and" |
| Column 13, line 11 | delete "Thus no, one" and insert -- Thus, no one -- |
| Column 13, line 63 | after "cross-sections" insert a period -- . -- |
| Column 16, line 12 | delete "a" |

UNITED STATES PATENT AND TRADEMARK OFFICE
CERTIFICATE OF CORRECTION

PATENT NO. : 5,127,906
DATED : July 7, 1992
INVENTOR(S) : Maurice J. Landry, Jr. and Frederick L. Plouff It is certified that error appears in the above-indentified patent and that said Letters Patent is hereby corrected as shown below:

Column 16, line 16, delete "insert means"

Signed and Sealed this

Sixteenth Day of May, 1995

Attest:

BRUCE LEHMAN

Attesting Officer

Commissioner of Patents and Trademarks